United States Patent [19]
Neilan et al.

[11] Patent Number: 5,334,762
[45] Date of Patent: Aug. 2, 1994

[54] METHOD FOR ACCELERATING OXIME PRODUCTION

[75] Inventors: James P. Neilan, Bear, Del.; Donald J. Gosciniak, West Chester, Pa.

[73] Assignee: Zeneca Inc., Wilmington, Del.

[21] Appl. No.: 13,278

[22] Filed: Feb. 4, 1993

[51] Int. Cl.$^5$ ............................................. C07C 249/08
[52] U.S. Cl. .................................................... 564/259
[58] Field of Search .................... 502/152; 556/87, 94, 556/95; 564/259

[56] References Cited

U.S. PATENT DOCUMENTS

| | | | |
|---|---|---|---|
| 3,470,220 | 9/1969 | Moedritzer et al. | 556/87 |
| 3,808,275 | 4/1974 | Hirose et al. | 260/566 A |
| 4,133,834 | 1/1979 | Pickens | 260/566 A |
| 4,638,096 | 1/1987 | Virnig | 568/433 |
| 5,145,976 | 9/1992 | Nichols et al. | 556/88 |

*Primary Examiner*—Peter O'Sullivan
*Attorney, Agent, or Firm*—Panitch, Schwarze, Jacobs & Nadel

[57] ABSTRACT

A method for preparing oximes where an aldehyde or ketone is reacted with hydroxylamine or its salt in the presence of a catalytic amount of an organotin(IV) compound such as monoalkyltin(IV), dialkyltin(IV) and aryltin(IV). The organotin(IV) compound is represented by the formula I:

$$(R^1)_n SnX_{m-n} \qquad (I)$$

where $R^1$ is independently selected from alkyl of 1 to 18 carbons or aryl, X is halogen, oxygen, hydroxyl, $OR^1$, $R^2CO_2-$, $R^2O_2C-(Z)_y-CO_2-$ or $R^2CO_2(CH_2)_yS-$, $R^2$ is alkyl of 1 to 18 carbons or aryl, Z is selected from $CH_2$ or $CH=CH$, where y is 0 to 6, n is 1 or 2 and m is 4 except that when X is oxygen, n is 2 and m is 3. Exemplary of the organotin(IV) compounds are butyltin tris(2-ethylhexanoate), dibutyltin diacetate and diphenyltin dichloride.

9 Claims, No Drawings

METHOD FOR ACCELERATING OXIME PRODUCTION

FIELD OF THE INVENTION

The present invention relates to a method for accelerating the rate of production of oximes from aldehydes or ketones and hydroxylamine.

BACKGROUND OF THE INVENTION

Oximes are important organic derivatives of hydroxylamine. The compounds are amphoteric and have many uses. For example, the use of 2-hydroxyarylaldoximes (salicylaldoximes) as extractants in the hydrometallurgical recovery of metals from metal ores is well known and has been practiced commercially for a number of years. More specifically, the compound 5-nonylsalicylaldehyde oxime is used in the mining industry for the hydrometallurgical recovery of copper from crude ores.

Oximes are prepared by the direct reaction of hydroxylamine with aldehydes and ketches. However, long cycle times are required to achieve high yields. Exemplary of the present state of the art is the oximation reaction of 5-nonylsalicylaldehyde which is carried out at 45° C. by the addition of sodium carbonate to a two-phase system consisting of a toluene solution of aldehyde and an aqueous solution of hydroxylamine sulfate. Using a feed stock of 90% aldehyde strength, cycle times of approximately 8 hours are required to convert greater than 98% of the aldehyde to the oxime. The long cycle times required to obtain high yields significantly slow the overall manufacturing process. Thus, it is desirable to reduce the cycle time of the oximation process.

Attempts have been made to improve the yields and increase the rate of oximation reactions. U.S. Pat. No. 4,133,834 discloses the use of soluble iron compounds to accelerate the formation of alpha- and beta-hydroxy oximes from the corresponding carbonyl compounds. Catalytic amounts of ferrous ($Fe^{2+}$) and ferric ($Fe^{3+}$) contributing compounds are used. However, relatively high levels of catalyst are required and the iron compounds impart an objectionable color to the oxime product.

Another process for producing oximes is disclosed in U.S. Pat. No. 3,808,275 in which a variety of inorganic tin-containing compounds were used to improve the yield of oximations. The tin-containing compounds disclosed also include organotin compounds such as trialkyl tin, but no examples are given. Exemplary of the inorganic tin compounds is the use of 0.1 g of sodium $\alpha$-stannate ($Na_2SnO_3 \cdot 3 H_2O$) in the oximation of 91 g of cyclododecanone to cyclododecanoneoxime. The conversion of cyclododecanone increased to 98.1% as opposed to 94.6% in the absence of sodium $\alpha$-stannate. Yields of the oxime were increased from 98.3% to 99.2%. However, relatively long cycle times are required to achieve the increased conversion and yield.

While some of the above-referenced catalysts are commercially useful in oxime production, a goal of the industry continues to be to develop better catalysts that can be used in lower amounts and improve cycle time or reaction rate and not interfere with the oxime product end use.

SUMMARY OF THE INVENTION

According to the present invention, the cycle time or reaction rate of producing oximes can be significantly improved. This improvement is achieved by reacting an aldehyde or ketone with hydroxylamine or a salt thereof in the presence of a catalytic amount of an organotin(IV) compound selected from the group consisting of monoalkyltin(IV), dialkyltin(IV) and aryltin(IV) compounds.

In a preferred embodiment of the present invention, the above method is carried out in the presence of a catalytic amount of an organotin(IV) compound selected from the group consisting of dibutyltin diacetate, dibutyltin dilaurate, dibutyltin di-2-ethylhexanoate, dibutyltin-S-S-bis(isooctylmercaptoethanoate), dibutyl tin oxide, dibutyltin dichloride, diphenylbutyltin tris-(2-ethylhexanoate), dibutyltin maleate, butyl tin tris(2-ethylhexanoate) and butyltin S,S'-tris(isooctylmercaptoethanoate) and is present in an amount of at least about 0.005%.

In another preferred embodiment, the aldehyde substrate is a 2'-hydroxyarylaldehyde, preferably salicylaldehyde or 5-nonylsalicylaldehyde.

DETAILED DESCRIPTION OF THE INVENTION

The method of the present invention is useful for accelerating the rate of oximation of aromatic and aliphatic ketones and aldehydes. Preferred substrates for oximation by the method of the invention are 2'-hydroxyarylaldehydes. Most preferably, the oximation substrates are salicylaldehyde or 5-nonylsalicylaldehyde.

The aromatic ketone substrates can include acetophenone and 2'-hydroxyacetophenone. The aromatic aldehyde substrates can also include benzaldehyde.

Accelerated oximation is achieved by reacting an aldehyde or ketone with hydroxylamine or a salt thereof in the presence of a catalytic amount of an organotin(IV) compound selected from the group consisting of monoalkyltin(IV), dialkyltin(IV) and aryltin(IV) compounds. The organotin(IV) compound is represented by the formula:

$$(R^1)_n SnX_{m-n} \qquad (I)$$

where $R^1$ is independently selected from alkyl of 1 to 18 carbons or aryl, X is halogen, oxygen, hydroxyl, $OR^1$, $R^2CO_2-$, $R^2O_2C-(Z)_y-CO_2-$, or $R^2CO_2(CH_2)_yS-$, $R^2$ is alkyl of 1 to 18 carbons or aryl, Z is selected from $CH_2$ or $CH=CH$, where y is 0 to 6, n is 1 or 2 and m is 4 except that when X is oxygen, n is 2 and m is 3.

Preferred compounds for use in the method of the invention include dibutyltin diacetate, dibutyltin dilaurate, dibutyltin di-2-ethylhexanoate, dibutyltin-S-S-bis-(isooctylmercaptoethanoate), dibutyltin oxide, dibutyltin dichloride, diphenylbutyltin tris-(2-ethylhexanoate), dibutyltin maleate, butyltin tris(2-ethylhexanoate) and butyltin S,S'-tris(isooctylmercaptoethanoate).

The organotin(IV) compounds are preferably used in amounts of at least about 0.005% (based on aldehyde). All catalyst percent references used hereinafter are wt/wt % based on aldehyde. Most preferably, the organotin(IV) compounds are used in amounts from about 0.005% to about 0.2%. Larger amounts of catalyst can be used if desired.

The salts of hydroxylamine for use in the present process include .HCl, .HBr, .H$_2$SO$_4$, .H$_3$PO$_4$ and .HNO$_3$, preferably .H$_2$SO$_4$.

Preferably, the reaction is carried out in a two-phase toluene/aqueous system. Other organic solvents which form a heterogeneous system with water such as, for example, cyclohexane, methylcyclohexane, hydrocumene, benzene, xylene, carbon tetrachloride, chloroform and tetrachloroethane can also be used.

The reaction temperature is generally 30° C. to 150° C., preferably about 45° C. The reaction temperature may vary depending upon the specific aldehyde or ketone substrate used.

Aldehyde oximations preferably have a pH of about 3 to about 8 at completion and ketone oximations have a pH of about 6 to about 12 upon completion. Typically, the final pH of the aqueous phase is about 6.8 to about 8.0. The pH may be controlled by addition of inorganic compounds such as ammonia, sodium hydroxide, potassium hydroxide, sodium carbonate, potassium carbonate and organic basic compounds such as triethylamine or cyclohexylamine.

The reaction may be conducted either batchwise or continuously at pressure ranges from about atmospheric pressure to about 10 kg/cm$^2$.

Recovery of the oxime product can be achieved by acidification of the organic layer followed by aqueous extraction of the organic layer. The organic solvent is removed by conventional techniques to yield the oxime product.

The present method will now be illustrated in more detail by reference to the following, specific, non-limiting examples.

EXAMPLE 1

Oximation of 5-Nonylsalicylaldehyde

A 500 ml 4-necked round bottom flask was charged with 65.9 g 5-nonylsalicylaldehyde (91% active, 0.242 mole) in 48 ml toluene. The contents were heated with stirring to 45° C. under a nitrogen blanket.

The catalysts indicated in Table 1 were prepared by serial dilutions of stock solutions with toluene. A 0.1 ml aliquot of the diluted catalyst was added to the reaction mixture to give the final weight percent of the catalyst in the reaction mixture as indicated in Table 1.

A solution containing 21.8 g (0.133 mole) hydroxylamine sulfate in 35 ml water was preheated to 45° C. and added to the reaction flask over approximately 30 seconds. A solution containing 14.5 g (0.136 mole) sodium carbonate in 35 ml water as an acid-binding agent was added dropwise over a period of 3-5 minutes. Gas evolution occurred (carbon dioxide) and the temperature decreased to approximately 38° C. The reaction mixture was warmed to 45° C. Known amounts of the reaction mixture were removed at various time intervals, diluted with acetone and analyzed by gas chromatography (GC) for aldehyde starting material. The analysis was performed on a 6' packed column of 2% butanediol succinate on Chromasorb W ® isothermally at 180° C. using a flame ionization detector. The oximation reaction was allowed to proceed until the GC analysis indicated that less than 2% of the aldehyde starting material remained.

The stirring was halted and the aqueous layer removed. The organic layer was stirred with 25 ml of 5.6% sulfuric acid at 45° C. for 15 minutes. The acid layer was removed and the organic layer washed three times with 35 ml water. The toluene was removed by rotary evaporation at 60° C. for 30 minutes at 25 mm Hg and then for 30 minutes at 2-5 mm Hg. A viscous yellow oil was recovered, weighed and analyzed for oxime strength by copper uptake potentiometric titration.

The effectiveness of various tin-containing compounds and iron complexes as catalysts is shown in Table 1. "PPM METAL" reflects parts per million tin in the reaction mixture.

Reaction Nos. 2-12 are exemplary of oximations using organotin compounds per the method of the present invention. Reaction Nos. 2-6 employed dibutyltin diacetate; Reaction No. 7 employed dibutyltin dilaurate; Reaction No. 8 employed dibutyltin oxide; Reaction Nos. 9 and 10 employed butyltin tris(2-ethylhexanoate); Reaction No. 11 employed dibutyltin dichloride; and Reaction No. 12 employed diphenyltin dichloride. Although dialkyltin alkoxides were not screened for catalytic activity, it is expected that they would be active as catalysts based on their structural similarities to the organotin(IV) compounds screened in Reaction Nos. 2-12.

Reaction Nos. 13-21 are exemplary of trialkyl tin complexes and inorganic tin compounds previously known as catalysts. Reaction Nos. 13 and 14 employed tributyltin chloride; Reaction No. 15 employed bis(tributyltin); Reaction No. 16 employed bis(tributyltin) oxide; Reaction No. 17 employed tin(IV) acetate; Reaction No. 18 employed tin(II) acetate; Reaction No. 19 employed tributyltin acetate; and Reaction Nos. 20 and 21 employed sodium stannate(IV) trihydrate.

The iron-containing catalysts used in Reaction Nos. 22 and 23, namely iron(II) acetate and iron(III) sulfate pentahydrate, respectively, were also previously known as catalysts.

The results in Table 1 indicate that use of catalytic amounts of organotin(IV) compounds per the method of the present invention (Reaction Nos. 2-12) resulted in reactions which were generally complete within two hours at a 0.02% level of organotin catalyst. The organotin compounds tested in Reaction Nos. 2-12 show a significant advantage over other types of tin compounds such as the trialkyl tin complexes of Reaction Nos. 13, 14, 15, 16 and 19, the tin acetates of Reaction Nos. 17 and 18 and the inorganic tin compounds of Reaction Nos. 20 and 21.

At levels of 0.02% dibutyltin diacetate (Reaction No. 3), greater than 98% of 5-nonylsalicylaldehyde was converted to the oxime within two hours. In contrast, Reaction Nos. 13-21 employing known tin catalysts outside the scope of the present invention at 0.02% require reaction times of 5 to 7.5 hours to achieve comparable to lower levels of aldehyde conversion. For example, use of sodium stannate(IV) trihydrate (Reaction No. 20) or bis(tributyltin) oxide (Reaction No. 16) at 0.02% levels for 7.5 and 6 hours, respectively, did not achieve the same level of conversion as the method of the present invention. In Reaction No. 21, although a ten-fold greater level of sodium stannate(IV) trihydrate was used, a 5-hour cycle time was still required to convert approximately 97% of the aldehyde.

Reaction Nos. 22 and 23, while showing rate enhancement over the control Reaction No. 1, required higher levels of the iron complex catalysts and longer reaction times as compared to the method of the present invention. Moreover, the final reaction product using the iron complexes had an objectionable color.

TABLE 1

| REACTION NO. | CATALYST | CATALYST AMOUNT | PPM METAL | CYCLE TIME | OXIME ASSAY (%) | YIELD (%) |
|---|---|---|---|---|---|---|
| 1 | none | 0% | 0 | 8 hrs | 90.0 | 99.0 |
| 2 | $(CH_3CO_2)_2Sn[(CH_2)_3CH_3]_2$ | 0.2% | 670 | 0.5 hrs | 89.3 | 98.3 |
| 3 | $(CH_3CO_2)_2Sn[(CH_2)_3CH_3]_2$ | 0.02% | 67 | 2 hrs | 89.2 | 98.7 |
| 4 | $(CH_3CO_2)_2Sn[(CH_2)_3CH_3]_2$ | 0.01% | 34 | 3 hrs | 89.1 | 97.5 |
| 5 | $(CH_3CO_2)_2Sn[(CH_2)_3CH_3]_2$ | 0.005% | 17 | 4 hrs | 89.0 | 99.0 |
| *6 | $(CH_3CO_2)_2Sn[(CH_2)_3CH_3]_2$ | 0.02% | 67 | 1.5 hrs | 72.0 | 99.4 |
| 7 | $[CH_3(CH_2)_{10}CO_2]_2Sn[(CH_2)_3CH_3]_2$ | 0.02% | 29 | 3 hrs | 90.1 | 98.6 |
| 8 | $[CH_3(CH_2)_3]_2Sn(=O)$ | 0.02% | 73 | 2 hrs | 90.0 | 99.1 |
| 9 | $[CH_3(CH_2)_3CH(C_2H_5)CO_2]_3Sn(CH_2)_3CH_3$ | 0.2% | 330 | 1 hr | 90.2 | 99.7 |
| 10 | $[CH_3(CH_2)_3CH(C_2H_5)CO_2]_3Sn(CH_2)_3CH_3$ | 0.02% | 33 | 2.5 hrs | 89.3 | 98.9 |
| 11 | $[CH_3(CH_2)_3]_2SnCl_2$ | 0.02% | 78 | 2 hrs | N.D. | N.D. |
| 12 | $(C_6H_5)_2SnCl_2$ | 0.02% | 69 | 4 hrs | 88.6 | 97.3 |
| 13 | $[CH_3(CH_2)_3]_3SnCl$ | 0.2% | 674 | 3 hrs | N.D. | N.D. |
| 14 | $[CH_3(CH_2)_3]_3SnCl$ | 0.02% | 67 | 5 hrs | 89.7 | 97.6 |
| 15 | $\{[CH_3(CH_2)_3]_3Sn\text{-}\}_2$ | 0.02% | 82 | 6 hrs | 89.0 | 97.4 |
| 16 | $[CH_3(CH_2)_3]_3SnOSn[(CH_2)_3CH_3]_3$ | 0.02% | 80 | 6 hrs | 89.8 | 98.4 |
| 17 | $(CH_3CO_2)_4Sn$ | 0.02% | 67 | 6 hrs | 90.4 | 98.6 |
| 18 | $(CH_3CO_2)_4Sn$ | 0.02% | 108 | 5 hrs | 88.8 | 95.6 |
| 19 | $CH_3CO_2Sn[(CH_2)_3CH_3]_3$ | 0.02% | 68 | 7 hrs | 89.9 | N.D. |
| 20 | $Na_2SnO_3 \cdot 3H_2O$ | 0.02% | 68 | 7.5 hrs | 90.1 | 97.3 |
| 21 | $Na_2SnO_3 \cdot 3H_2O$ | 0.2% | 680 | 5 hrs | 88.7 | 96.9 |
| 22 | $(CH_3CO_2)_2Fe$ | 0.08% | 119 | 3 hrs | 89.3 | 97.6 |
| 23 | $Fe_2(SO_4)_3 \cdot 5H_2O$ | 0.08% | 119 | 3 hrs | 90.4 | N.D. |

N.D. = not determined
*Starting aldehyde was 70% pure, balance was nonylphenol.

EXAMPLE 2

Oximation of Carbonyl Substrates

A 250 ml 3-necked round bottomed flask was charged with 0.1 mole of either salicylaldehyde (12.2 g), benzaldehyde (10.6 g), acetophenone (12.0 g) or 2'-hydroxyacetophenone (13.6 g) in 45 ml toluene. To this solution was added 1.0 g naphthalene as an internal standard.

Control reactions (without organotin(IV) catalyst) were performed by adding a solution of hydroxylamine sulfate (9.0 g, 0.055 mole) in 15 ml water and heating the mixture with stirring to 45° C. followed by the addition of a solution of sodium carbonate (5.8 g, 0.055 mole) in 15 ml water added over 2-3 minutes. Catalyzed reactions were performed in the presence of 0.01 g of dibutyltin diacetate which was added to the reaction in 0.1 ml of toluene prior to addition of hydroxylamine sulfate. The reaction was sampled periodically by halting agitation and removing an aliquot as in Example 1. Depletion of the starting material, i.e., conversion to the corresponding oxime, was determined by GC analysis on a 30 meter Supelco SPB-5 capillary column with a flame ionization detector. After injection, the column temperature was maintained at 100° C. for 5 minutes, increased 5° C./minute to 250° C. and then maintained at 250° C. for 5 minutes. The data are shown in Table 2.

Reaction Nos. 1, 3, 5 and 7 were the controls for reaction Nos. 2, 4, 6 and 8, respectively.

The results in Table 2 indicate that use of catalytic amounts of organotin(IV) compounds per the method of the present invention increase oximation rates of carbonyl-containing substrates such as arylaldehydes and arylketones over reactions lacking catalysts. Approximately two- and four-fold increases in percent conversion of 2'-hydroxyacetophenone and acetophenone, respectively, were observed. Conversion rates of 99% to 100% for the arylaldehydes, salicyclaldehyde and benzaldehyde, were achieved in the presence of organotin(IV) catalyst.

TABLE 2

| REACTION # | REACTANT | REACTANT WEIGHT | DIBUTYLTIN DIACETATE CATALYST | TIME (HRS) | CONVERSION |
|---|---|---|---|---|---|
| 1 | Salicylaldehyde | 12.2 g | 0% | 1.0 | 82% |
| 2 | Salicylaldehyde | 12.2 g | 0.08% | 1.0 | 99% |
| 3 | Benzeldehyde | 10.6 g | 0% | 0.5 | 86% |
| 4 | Benzeldehyde | 10.6 g | 0.09% | 0.5 | 100% |
| 5 | Acetophenone | 12.0 g | 0% | 5.0 | 10% |
| 6 | Acetophenone | 12.0 g | 0.08% | 5.0 | 37% |
| 7 | 2'-hydroxy-acetophenone | 13.6 g | 0% | 5.0 | 16% |
| 8 | 2'-hydroxy-acetophenone | 13.6 g | 0.07% | 5.0 | 31% |

The present invention may be embodied in other specific forms without departing from the spirit or essential attributes thereof and, accordingly, reference should be made to the appended claims, rather than to the foregoing specification as indicating the scope of the invention.

We claim:

1. A method for preparing oximes, comprising:
reacting an aldehyde or ketone with hydroxylamine or a salt thereof in the presence of a catalytic amount of an organotin(IV) compound selected from the group consisting of monoalkyltin(IV), dialkyltin(IV) and aryltin(IV) compounds.

2. The method of claim 1 wherein the organotin(IV) compound is represented by the formula:

$$(R^1)_n SnX_{m-n} \qquad (I)$$

where $R^1$ is independently selected from alkyl of 1 to 18 carbons or aryl, X is halogen, oxygen, hydroxyl, $OR^1$, $R^2CO_2-$, $R^2O_2C-(Z)_y-CO_2-$, or $R^2CO_2(CH_2)_yS-$, $R^2$ is alkyl of 1 to 18 carbons or aryl, Z is selected from $CH_2$ or $CH=CH$, where y is 0 to 6, n is 1 or 2 and m is 4 except that when X is oxygen, n is 2 and m is 3.

3. The method of claim 1 wherein the organotin(IV) compound is selected from the group consisting of dibutyltin diacetate, dibutyltin dilaurate, dibutyltin di-2-ethylhexanoate, dibutyltin-S-S-bis(isooctylmercaptoethanoate), dibutyl tin oxide, dibutyltin dichloride, diphenylbutyltin tris-(2-ethylhexanoate), dibutyltin maleate, butyl tin tris(2-ethylhexanoate) and butyltin S,S'-tris(isooctylmercaptoethanoate).

4. The method of claim 1 wherein the aldehyde is a 2'-hydroxyarylaldehyde.

5. The method of claim 4 wherein the 2'-hydroxyarylaldehyde is salicylaldehyde or 5-nonylsalicylaldehyde.

6. The method of claim 1 wherein the aldehyde is benzaldehyde.

7. The method of claim i wherein the ketone is acetophenone or 2'-hydroxyacetophenone.

8. The method of claim 1 wherein the organotin(IV) compound is present in an amount of at least about 0.005%.

9. The method of claim 8 wherein the organotin(IV) compound is present in an amount of about 0.005% to about 0.2%.

* * * * *